United States Patent [19]

Taniguchi

[11] Patent Number: 5,449,551
[45] Date of Patent: Sep. 12, 1995

[54] HIGHLY WATER ABSORBENT FIBROUS WEB AND A PROCESS FOR PRODUCING THE SAME

[75] Inventor: Kenji Taniguchi, Minamisaitama, Japan

[73] Assignee: Kawano Paper Co., Ltd., Japan

[21] Appl. No.: 70,864

[22] Filed: Jun. 3, 1993

[51] Int. Cl.$^6$ .......................... A61K 9/70; B23B 9/06; B23B 23/14
[52] U.S. Cl. .................................. 428/288; 428/289; 428/290; 428/291
[58] Field of Search ............... 428/153, 154, 288, 289, 428/290, 291, 486, 487, 511, 537.5; 162/DIG. 3, DIG. 6, 111, 112

[56] References Cited

U.S. PATENT DOCUMENTS

| | | | |
|---|---|---|---|
| 3,953,638 | 4/1976 | Kemp | 428/154 |
| 4,277,529 | 7/1981 | Friedman | 428/511 X |
| 4,413,995 | 11/1983 | Korpman | 428/289 X |
| 4,500,585 | 2/1985 | Erickson | 428/153 X |
| 4,537,807 | 8/1985 | Chan et al. | 428/290 X |
| 4,601,938 | 7/1986 | Deacon et al. | 428/153 |
| 4,764,418 | 8/1988 | Kuenn et al. | 428/290 X |
| 4,846,932 | 7/1989 | Karita et al. | 428/537.5 X |
| 5,059,282 | 10/1991 | Ampulski et al. | 428/153 X |
| 5,164,046 | 11/1992 | Ampulski et al. | 428/153 X |

FOREIGN PATENT DOCUMENTS

| | | |
|---|---|---|
| 2127595 | 5/1990 | Japan . |
| 2224626 | 9/1990 | Japan . |
| 3900 | 1/1991 | Japan . |
| 3180598 | 8/1991 | Japan . |
| 523262 | 2/1993 | Japan . |
| 5106188 | 4/1993 | Japan . |

*Primary Examiner*—Jenna L. Davis

[57] ABSTRACT

A fibrous web such as paper and non-woven fabrics, which contains: at least one kind of materials selected from salts having hygroscopicity, and polyhydric alcohols and sugars having hygroscopicity; at least one kind of materials mentioned above and adhesive paste having water retention; or materials of either of the above two choices and oil materials, in a 1.0 to 300 wt % based on the fibrous web weight. Such chemical materials are preferably selected from food, food additives and materials listed in the Japanese Standards of Cosmetic Ingredients and the Pharmacopoeia of Japan, to ensure safety in use of the web. The fibrous web are prepared by impregnating such materials in fibrous web which is wet in web-making process by spraying, etc., or fibrous web obtained after web-making process. The chemical materials make increase the moisture content of the web by absorbing and retaining moisture in air, and enhance the softness and feel to skin of the fibrous web. Therefore, there can be provided a fibrous web which is unsusceptible to humidity change of air, and which lints less web waste, by enhancing the adhesiveness between fibers.

1 Claim, 1 Drawing Sheet

HIGHLY WATER ABSORBENT FIBROUS WEB AND A PROCESS FOR PRODUCING THE SAME

BACKGROUND OF THE INVENTION

1. Field of the Invention

The present invention relates to a fibrous web such as paper and non-woven fabrics having a high water containability, and a process for producing the same, specifically relates to a fibrous web having a high water containability which is highly safe in use, soft and excellent in feel to skin, and lints little web waste in its producing process, as well as is suitable for food, sanitary and household products.

2. Description of the Related Art

In the household paper such as tissue paper and toilet tissue and other fibrous web, the softening agents have been used occasionally in order to, for example, soften their feel.

The softening agent acts not only as a plasticizer of a wet strength-reinforcing agent for paper (i.e., a chemical agent to maintain the strength of paper at wet condition), but also as follows.

That is, in such softening agents have hydrophilic groups and lipophilic groups, and the hydrophilic groups are adsorbed to cellulose, whereas the lipophilic groups orient outside of the cellulose. Accordingly, the cellulose becomes surrounded with the lipophilic groups, resulting in flexibility as well as smoothness of the surface. Furthermore, the smoothness between cellulose becomes good and the resistance between cellulose becomes less, and consequently, the feel to skin becomes smooth and soft. In this state, the hydrogen bonds in the fiber are sealed and the smoothness between fibers are enhanced to make the feel soft.

The softening agents having above-mentioned activities may be applied by mixed with the above-mentioned raw materials of fibrous web such as tissue paper to web-make, or by impregnating to web which is wet, i.e., after the web formation and before drying, or web which is obtained after web-making and before drying (hereinafter, referred to as the external addition method).

As to the softening agent, there have been known, for example, surfactants, wax emulsions (i.e., those which are obtained by emulsifying waxes with surfactants and in which the waxes act as the above-mentioned lipophilic groups), and reactive softening agents (i.e., those which react with cellulose strongly and make aliphatic hydrocarbons orient surrounding fibers regularly).

In addition, recently, a silicone-based softening agent has been developed in order to give tissue paper a soft, silky and flannel-like tactile feel as well as high bulk property (referred to Japanese Patent Application Laid-open Nos. 224626/1990 and 900/1991).

On the other hand, fibrous webs used for food, sanitary and household products are required to be highly safe in use, since they should contact with food, mucosa, skin, and the like.

However, the conventional softening agents described above are chemically synthesized products, and there is some fear in safety of the webs to which such softening agents are applied to the webs in high concentration.

As mentioned above, the conventional softening mechanism consists in the inhibition of hydrogen bond formation between fibers, in which the lipophilic groups of the softening agent orient outside of cellulose, and the hydrophilic groups are adsorbed on the cellulose. Accordingly, the interlacing or binding of fibers are impaired and the some fibers fall out, resulting in increase of linting of web waste such as paper edge dust and fiber dust.

Further, the lipophilic groups orienting outside of cellulose provide the fiber a water repellency, and impair its water adsorption property. Therefore, the water adsorption property essentially needed to tissue paper, toilet tissues, etc. made of such fibers is also impaired.

According to the above problems, the conventional softening agents have been limited in the amount to be applied to fibrous webs, and can not provide an excellent softness with the resulting fibrous webs such as tissue paper and toilet tissues.

SUMMARY OF THE INVENTION

It is an object of the present invention to solve such problems mentioned above, and to provide a fibrous web such as paper and non-woven fabrics having a high water containability which has a high safety in use, softness and an excellent feel to skin, as well as is appropriate to use for food, sanitary and household products.

Another object of the present invention is to provide a fibrous web such as paper and non-woven fabrics having a high water containability which has a humectant property as well as lints less web waste.

A further object of the present invention is to provide a method for producing a fibrous web from which paper and non-woven fabrics having a high water containability can be prepared easily.

In order to achieve the above objects, the fibrous web according to the present invention is characterized in containing one group selected from the class consisting of:

(1) at least one kind of materials selected from the group consisting of salts having a hygroscopicity, and polyhydric alcohols and sugars having a hygroscopicity;

(2) materials of above (1) and adhesive paste having a water retention; and (3) materials of either group of above (1) or (2), and oil materials, in a 1.0 to 300 wt % based on the fibrous web weight.

The fibrous web of the present invention is also characterized in that the salts having a hygroscopicity, polyhydric alcohols and sugars having a hygroscopicity, adhesive paste having a water retention, and oil materials to be applied are those selected from food, food additives and materials listed in the Japanese Standards of cosmetic Ingredients and the Pharmacopoeia of Japan.

The fibrous web of the present invention is produced by the external addition method, in which one group selected from the groups of above (1) to (3) is impregnated in wet web which is obtained after web formation and before drying in the fibrous web-making process or web obtained after the fibrous web-making process.

DETAILED DESCRIPTION OF THE INVENTION

Figure 1:
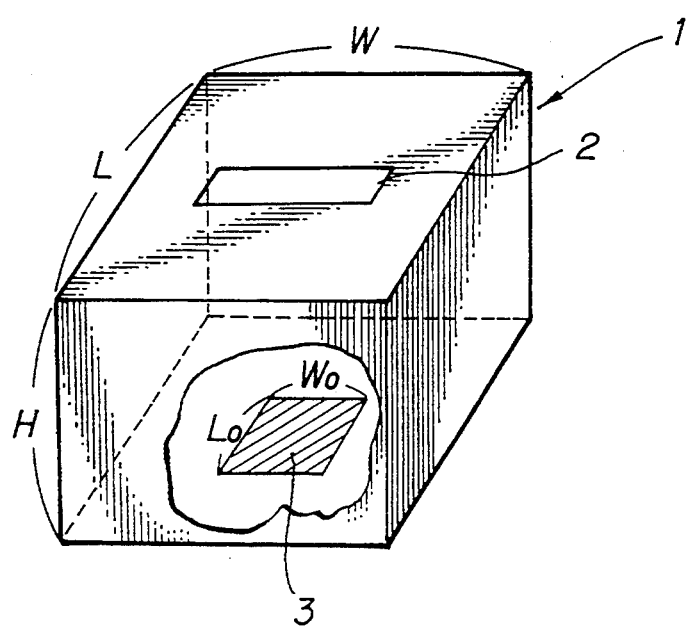
FIG. 1 illustrates the apparatus for observation of linting condition of web waste, i.e., paper edge dust, which is used in Examples to demonstrate the effect of the fibrous web of the present invention.

Examples of salts having a hygroscopicity to be applied to the fibrous web of the present invention include sodium chloride, calcium chloride, potassium pyrophosphate, sodium metaphosphate, potassium polyphosphate, sodium polyphosphate, and so on.

Examples of polyhydric alcohols and sugars having a hygroscopicity include glycerol, diglycerol, D-sorbit, maltitol, reducing malt sugar syrup, reducing starch hydrolysate, and so on.

Examples of adhesive paste having a water retention include sodium alginate, sodium polyacrylate, methylcellulose, propylene glycol alginate ester, sodium cellulose glycolate (CMC), calcium cellulose glycolate, sodium starch glycolate, sodium starch phosphate ester, casein, sodium casein, and so on.

The salts having a hygroscopicity, polyhydric alcohols and sugars having a hygroscopic property and adhesive paste having a water retention mentioned above provide the fibrous web of the present invention with hygroscopicity, softness and good feel to skin, or enhance such properties of the fibrous web (accordingly, these additives are collectively referred to hereinafter as "hygroscopicity, softness, etc.—giving agents"). The fibrous web of the present invention may contain at least one kind of the chemical materials having a hygroscopicity.

In the fibrous web of the present invention, the content of the hygroscopicity, softness, etc.—giving agents to be applied is preferably within the range from 1.0 to 300 wt % based on the web weight. When the content is too small, an noticeable effect by such agents can not be provided, whereas it is uneconomic to contain a too large amount of such agents because of saturation of the effect.

Furthermore, in case where the resulting product of the present fibrous web is paper such as tissue paper required to have an excellent feel to skin, the content of the hygroscopicity, softness, etc.—giving agents to be applied is preferably within the range from 1.0 to 100 wt %. When the content is less than 1.0 wt %, the resulting paper can not be improved in feel to skin. On the the hand, when more than 100 wt %, the resulting paper is inferior in feel in use because of too much of moisture content. However, in case where the resulting products is non-woven fabrics, the content may be within the range from 1.0 to 300 wt %, since the latter problem is not occurred.

Additionally, in the fibrous web of the present invention, oil materials can be additionally contained, as required, in order to improve the smoothness and tactile feel of the fibrous webs.

Examples of such oil materials include hydrocarbons such as liquid paraffin, squalane, and so on; vegetable oils such as olive oil, tsubaki oil, castor oil, soybean oil, and so on; waxes such as bees wax, carnauba wax, lanolin, and son on; and higher alcohols such as cetanol, stearyl alcohol, oleyl alcohol, and so on.

The content of the oil materials is preferably within the range from 0.1 to 30 wt % based on the the web weight. When the content of the oil materials is too small, a sufficient effect can not be provided. On the other hand, when the content is too much, a feel to skin of the resulting webs become worse.

The hygroscopicity, softness, etc.—giving agents and the oil materials used in the present invention are preferably those selected from food, food additives and materials listed in the Japanese Standards of Cosmetic Ingredients and the Pharmacopoeia of Japan to ensure a safety in use of the fibrous webs.

In the fibrous web of the present invention, a proper amount of surfactants can be blended, as required, in the mixture of the oil materials and the hygroscopicity, softness, etc.—giving agents described above or other materials described below in order to make the mixture homogeneously and in order to compensate a lowering of water absorbing property of the fibrous web resulted from containing of hydrophobic materials.

Examples of such surfactants include nonionic surfactants such as sucrose fatty acid ester, sorbitan fatty acid ester, glycerol fatty acid ester, polyoxyethylene lanoline alcohol ether, polyoxyethylenealkyl ether, polyoxyethylene fatty acid ester, and so on; and anionic surfactants such as fatty acid salts, alkylbenzenesulfonates, polyoxyethylene alkylether sulfates, and so on.

Additionally, in the fibrous web of the present invention, not only preservatives and antimolds but also the conventional softening agents described above can be blended in a proper amount, as required.

Examples of the preservatives and antimolds include sorbic acid, potassium sorbate, dehydroacetic acid, sodium dehydroacetate, benzoic acid, sodium benzoate, butyl parahydroxybenzoate, isobutyl parahydroxybenzoate, ethyl parahydroxybenzoate, propyl parahydroxybenzoate, isopropyl parahydroxybenzoate, and so on.

According to the present invention, the external addition method is adopted to prepare the fibrous web, in which the hygroscopicity, softness, etc.—giving agents and, if necessary, oil materials described above are impregnated in fibrous web which is wet, i.e., after web formation in the fibrous web-making process and before drying process, or impregnated in fibrous web obtained after the fibrous web-making and drying process.

When the external addition is carried out after drying process, a required amount of the hygroscopicity, softness, etc.—giving agents and, if necessary, the oil materials may be impregnated in the web (e.g., on the processing apparatus) by spraying their solutions on the web; by soaking the web in their solutions; or by printing them on the web by using of printing press.

According to the present invention, the salts having a hygroscopicity, polyhydric alcohols and sugars having a hygroscopicity, or adhesive paste having a water retention increase the moisture content of the fibrous web.

When the fibrous web of the present invention absorbs moisture, the moisture makes swell the fiber and releases the hydrogen bonds in the fiber, resulting in decrease of resistance against the external force. Moreover, the moisture acts as a lubricant between the fiber and the object (e.g., skin). In the present invention, these functions of the moisture improve softness and tactile feel of the fibrous web.

Generally speaking, humidity (i.e., moisture content) of paper or non-woven fabrics is balanced by a hygroscopic ability of paper or non-woven fabrics and humidity of the outer air.

In the fibrous web of the present invention, when adhesive paste having a water retention is applied with salts having a hygroscopicity and polyhydric alcohols and sugars having a hygroscopicity simultaneously, the evaporation rate of the moisture content once absorbed in the fibrous web from air becomes late due to water retaining property of the adhesive paste.

Therefore, in the fibrous web of the present invention in which adhesive paste is applied simultaneously with, the change of humidity (moisture content) becomes slow even in a weather condition where humidity of the outer air largely changes, and the function of moisture content concerning to the web softness and feel to skin as mentioned above is maintained for a long time.

In addition, when the above adhesive paste is applied simultaneously with, the adhesiveness between fibers is improved by the adhesive property of the adhesive paste, and the adhesive strength of the web is enhanced, and consequently, linting of web waste becomes less as well as the tactile feel (slimy feel) becomes improved.

Furthermore, in the present invention, the fibrous web in which the oil materials are applied simultaneously with is improved in smoothness and feel to skin.

As mentioned above, according to the present invention, there can be provided a fibrous web which is containable of high concentration of the hygroscopicity, softness, etc.—giving agents, since such agents are selected from highly safe materials. Accordingly, the fibrous web has more excellent softness and feel to skin than other conventional webs like the present fibrous web.

The fibrous web according to the present invention can further is ensured more highly safety in use by applying materials selected from food, food additives and materials listed in the Japanese Standards of Cosmetic Ingredients and the Pharmacopoeia of Japan as the hygroscopicity, softness, etc.—giving agents. Accordingly, the present invention can provide an extremely excellent web as the moisture control material for keeping freshness of food, sanitary products, and the like.

Further, the fibrous web according to the present invention has an excellent water retention, since the hygroscopicity, softness, etc.—giving agents to be applied are not tinged with lipophilicity and water repellency.

Furthermore, by applying the adhesive paste having a water retaining property as the hygroscopicity, softness, etc.—giving agent simultaneously with, the evaporation rate of moisture content once absorbed in the web becomes slow, and the excellent functions given by the moisture content can be maintained for a long time.

Consequently, by applying such adhesive paste simultaneously with according to the object of the intended use of the resulting fibrous web, there can be provided a web hard to be subjected to the influence of humidity change in the outer air.

The fibrous web according to the present invention can be processed into an excellent soft wet-type tissue paper by treatment of non-woven fabrics, which is hard to dry, has moist feel, and does not need a closed package which needed in conventional wet-type tissue for prevention from drying. In such wet-type tissue, the humectant components in the web transfers to skin and moistens the skin, and consequently, can give more excellent feel to skin and softness.

Moreover, according to the present invention, there can be provided a fibrous web having an extremely low linting of the so-called web waste, since the addition of the hygroscopicity, softness, etc.—giving agents not only protects from the inhibition of interlacing between fibers, but also enhances the adhesive strength between fibers.

Additionally, by containing the oil materials, as required, with the above hygroscopicity, softness, etc.—giving agents simultaneously, there can be provided a fibrous web having excellent smoothness and tactile feel.

EXAMPLES

1) Examples in which paper is used as a fibrous web:

Test samples were prepared as follows:

On both sides of a pair of tissue paper (a double ply) ("White Tissue": a trade name produced by Kawano Seishi K.K.; 200 pairs of tissue paper in a box) which is 13.0 $g/m^2$ by weighing and 200 mm long and 225 mm broad, the hygroscopicity, softness, etc.—giving agents of the present invention listed in Table 1 (in a single solution or a mixed solution of two or more of them) was sprayed uniformly by the hand spray in an amount shown in Table 1 based on the weight of a pair of tissue paper (26.0 $g/m^2$; defined as 100 wt %) and moistened, followed by drying process by using of the automatic thermo-hygrostat at 80°±2° C. for one hour.

Thus obtained test samples were leaved in stand in the conditioned box (humidity: 65±5%) at a temperature of 20°±5° C. for over eight hours. After reaching to equilibrium state, the samples were measured for various kinds of tests shown in Table 4. The results are also shown in Table 4 as the results of Examples 1 to 13, respectively.

2) Examples in which non-woven fabrics are used as fibrous webs:

Test samples were prepared as follows:

On both sides of non-woven fabric sheet ("Taiko TCF#503": a trade name produced by Futamura Kagaku Kogyo K.K.) which weight per unit area is 30 $g/m^2$ and is cut into 200 mm×160 mm, the hygroscopicity, softness, etc.—giving agents of the present invention listed in Table 2 (in a single solution or a mixed solution of two or more of them) were sprayed uniformly by using of the hand spray in an amount shown in Table 2 based on the weight of the non-woven fabric sheet (30.0 $g/m^2$; defined as 100 wt %) and moistened, followed by drying process in the same manner as above 1). After conditioning, the samples were measured for various kinds of tests shown in Table 5. The results are also shown in Table 5 as the results of Examples 14 and 15, respectively.

3) Comparative Examples

On the same tissue paper or non-woven fabric sheets as those used in 1) and 2), the chemical agents shown in Table 3 were sprayed instead of the hygroscopicity, softness, etc.—giving agents in the same manner as 1) and 2) in an amount shown in table 3, and then were subjected to drying and conditioning process in the same manner as 1) and 2). Thus obtained test samples were samples for Comparative Examples 1 and 2 (using of tissue paper) and Comparative Examples 3 and 4 (using of non-woven fabrics).

The samples were measured for various kinds of tests shown in Tables 4 and 5, respectively. The results are also shown in Tables 4 and 5, respectively.

Other two test samples were prepared for reference in the same manners as 1) and 2), respectively, except using only water instead of the hygroscopicity, softness, etc.—giving agents of the present invention shown in Tables 1 to 3. Thus obtained samples, i.e., Blank 1 (using of tissue paper) and Blank 2 (using of a non-woven fabric sheet), were measured for various kinds of tests shown in Tables 4 and 5, respectively. The results are also shown in Tables 4 and 5, respectively.

The chemical agents listed in Tables 1 to 3 are as follows:

potassium chloride: "Potassium Chloride (a reagent)", a trade name produced by Kokusan Kagaku K.K.;
  potassium pyrophosphate: "Potassium Pyrophosphate (a reagent)", a trade name produced by Kokusan Kagaku K.K.;
  sorbit: "Sorbitol-FP", a trade name produced by Nikken Kagaku K.K.;
  maltitol: "Maltitol (a reagent)", a trade name produced by Tokyo Kasei Kogyo K.K.;
  glycerol: "Food Additive Glycerin", a trade name produced by Asahi Denka Kogyo K.K.;
  liquid paraffin: "Crystol 70", a trade name produced by Esso Sekiyu K.K.;
  sodium alginate: "Duckalgin NSPM", a trade name produced by Kibun Food Chemifa Co., Ltd.;
  polyoxyethylene lanoline alcohol ether: "Lamigen ET-70" (HLB 14), a trade name produced by Daiichi Kogyo Seiyaku K.K.;
  sucrose fatty acid ester: "DK Ester F-140"(HLB 13), a trade name produced by Diichi Kogyo Seiyaku K.K.;
  sorbitan fatty acid ester: "Sorgen 50" (HLB 4.7), a trade name produced by Diichi Kogyo Seiyaku K.K.;
  parahydroxybenzoic acid ester: "Neo Mekkins", a trade name produced by Ueno Fine Chemicals Industry, Inc.

The "moisture absorption amount", W (%), in Tables 4 and 5 is a value determined by using the following formula 1:

$$W = \{(w2 - w1)/w1\} \times 100 \quad (1)$$

wherein w1 is a sample weight measured just after drying at 80°±2° C. for one hour, and w2 is a sample weight measured just after conditioning.

The "tactile feel" in Table 4 and 5 was evaluated by a sensory compared test by five panelists. In the test, the panelists scored the test samples, i.e., one having an excellent tactile feel was scored 3 points, one having a good tactile feel was scored 2 points, one having a little good tactile feel was scored 1 point, and one having a relatively bad tactile feel was scored zero point (the panelists could evaluate some samples among them as a same level), and the points scored by the five panelists were summed. The sample having a total points of 12 to 15 was judged as ⊚, the sample having a total points of 8 to 11 as ○, the sample having a total points of 4 to 7 as ▲, and the sample having a total points of zero to 3 as x.

The "humectant and softness" in Table 5 is a total judge of humectant property to skin and softness evaluated by a sensory compared test by five panelists, in which the panelists washed their hands by using of service water of ordinary temperature and toilet soap, and then dried with the each sample of non-woven fabrics in the same manner as with handkerchief. In the test, the panelists scored the test samples, i.e., one having a relatively good humectant and softness was scored 2 points, one having a little good humectant and softness was scored 1 points, and one having a relatively bad humectant and softness was scored zero point (the panelists could evaluate some samples among them as a same level), and the points scored by five panelists were summed. The sample having a total points of 7 to 10 was judged as ○, the sample having a total points of 3 to 6 as ▲, and the sample having a total points of zero to 2 as x.

The "tensile strength" in Table 4 is a value obtained by measurement of the longitudinal tensile strength of tissue paper according to the dry tensile strength test for tissue paper prescribed in JIS (Japanese Industrial Standard) S-3104.

The "water absorbency" in Tables 4 and 5 is a value measured according to the water absorption test prescribed in JIS S-3104.

The "paper edge dust" in Table 4 is the paper edge dust linting level evaluated by using the apparatus shown in FIG. 1.

In FIG. 1, box 1 having opening 2 on its upside is a size of W (=400 mm)×L (=350 mm)×H(=300 mm). FIG. 1 is drawn in lack of a part of side plate of box 1. On the inner bottom of box 1, paper sheet 3 of $W_0$(=100 mm)×$L_0$(=100 mm) painted its surface in black is placed, and a both-sided tapes are put on the painted surface closely in order to adsorb the paper edge dust.

Five pairs of each sample pinched their ends with fingers are inserted into box 1 from opening 2 and shook forward and backward in box 1 as their ends pinched with fingers, and then taken out. The adsorbing amount of paper edge dust of each sample is compared by visual observation. The sample of little paper edge is judged as ○, the sample of relatively much paper edge is judged as ▲, and the sample of much paper edge is 33.

According to the Examples, as apparently from Tables 4 and 5, the fibrous web of the present invention is more excellent in hygroscopicity, tactile feel, preventing property of paper edge dust linting, water (moisture) absorbing property, humectant property to skin and softness than samples of Comparative Examples and Blanks (with no treatment).

TABLE 1

| | Example No. (wt %) | | | | | | |
|---|---|---|---|---|---|---|---|
| | 1 | 2 | 3 | 4 | 5 | 6 | 7 |
| calcium chloride | 5.0 | 10.0 | | | | 5.0 | |
| potassium pyrophosphate | | | 10.0 | | | | |
| sorbit | | | | 5.0 | 15.0 | 5.0 | |
| maltitol | | | | | | | 10.0 |
| glycerol | | | | | | | |
| liquid paraffin | | | | | | | |
| sodium alginate | | | | | | | |
| polyoxyethylene-lanolin alcohol ether | | | | | | | |
| sucrose fatty acid ester | | | | | | | |
| sorbitan fatty acid ester | | | | | | | |
| parahydroxy-benzoic acid ester | | | | | | | |

| | Example No. (wt %) | | | | | |
|---|---|---|---|---|---|---|
| | 8 | 9 | 10 | 11 | 12 | 13 |
| calcium chloride | | | | | | |
| potassium pyrophosphate | | | | | | |
| sorbit | 2.5 | 2.5 | 2.5 | 2.5 | 4.0 | 4.0 |
| maltitol | | | | | | |
| glycerol | 1.5 | 1.5 | 2.5 | 2.5 | 4.0 | 4.0 |
| liquid paraffin | 1.0 | 1.0 | | 1.0 | 4.0 | 4.0 |
| sodium | | 0.1 | | | 0.1 | 0.1 |

TABLE 1-continued

| | | | | |
|---|---|---|---|---|
| alginate | | | | |
| polyoxyethylene-lanolin alcohol ether | 0.3 | 0.3 | 0.3 | 1.2 |
| sucrose fatty acid ester | | | 0.6 | |
| sorbitan fatty acid ester | | | 0.3 | |
| parahydroxy-benzoic acid ester | | | | 0.05 |

TABLE 2

| | Example No. (wt %) | |
|---|---|---|
| | 14 | 15 |
| calcium chloride | | |
| potassium pyrophosphate | | |
| sorbit | 10.0 | 4.0 |
| maltitol | | |
| glycerol | 10.0 | 4.0 |
| liquid paraffin | | 4.0 |
| sodium alginate | | 0.1 |
| polyoxyethylene lanolin alcohol ether | | 1.2 |
| sucrose fatty acid ester | | |
| sorbitan fatty acid ester | | |
| parahydroxy-benzoic acid ester | | 0.05 |

TABLE 3

| | Comparative Example No. (wt %) | | | |
|---|---|---|---|---|
| | 1 | 2 | 3 | 4 |
| liquid paraffin | 10.0 | 10.0 | 10.0 | 10.0 |
| polyoxyethylene lanolin alcohol ether | | 3.0 | | 3.0 |
| sucrose fatty acid ester | 1.5 | | 1.5 | |
| sorbitan fatty acid ester | 0.75 | | 0.75 | |

TABLE 4

| | moisture adsorption amount W (%) | tactile feel | tensile strength (gf) | paper edge dust | water absorbency (sec) |
|---|---|---|---|---|---|
| Example 1 | 10.9 | ○ | 317 | △ | 2.2 |
| 2 | 15.9 | ⊙ | 215 | ○ | 2.3 |
| 3 | 11.8 | ○ | 241 | ○ | 2.7 |
| 4 | 8.5 | △ | 327 | ○ | 2.1 |
| 5 | 10.1 | ⊙ | 222 | ○ | 2.3 |
| 6 | 11.1 | ⊙ | 231 | ○ | 3.1 |
| 7 | 8.1 | △ | 243 | ○ | 2.2 |
| 8 | 8.5 | ○ | 209 | △ | 2.3 |
| 9 | 8.9 | ⊙ | 255 | ○ | 2.5 |
| 10 | 9.0 | ○ | 216 | ○ | 1.6 |
| 11 | 8.9 | ⊙ | 203 | △ | 2.1 |
| 12 | 9.0 | ⊙ | 191 | ○ | 48.0 |
| 13 | 9.2 | ⊙ | 186 | ○ | 2.7 |
| Com. Example 1 | 5.8 | △ | 310 | △ | 60< |
| 2 | 5.8 | △ | 241 | × | 2.7 |
| Blank 1 | 5.6 | × | 312 | △ | 1.5 |

TABLE 5

| | moisture adsorption amount W (%) | tactile feel | water absorbency (sec) | humectant and softness |
|---|---|---|---|---|
| Example 14 | 18.1 | ⊙ | 1.3 | ○ |
| 15 | 14.0 | ⊙ | 1.4 | ○ |
| Com.Example 3 | 9.5 | △ | 60< | × |
| 4 | 8.3 | △ | 2.2 | △ |
| Blank 2 | 10.9 | × | 2.0 | × |

What is claimed is:

1. A highly water absorbent fibrous web, comprising a fibrous web having impregnated therein a hygroscopic composition in an amount of from 1.0 to 300 wt. % based on the weight of the fibrous web, said hygroscopic composition comprising glycerol, D-sorbit, and an oil material selected from the group consisting of liquid paraffin, squalene, olive oil, tsubaki oil, castor oil, soybean oil, bees wax, carnauba wax, lanolin, cetanol, stearyl alcohol, and oleyl alcohol.

* * * * *